(12) United States Patent
Suzuki

(10) Patent No.: US 11,485,813 B2
(45) Date of Patent: Nov. 1, 2022

(54) RESIN COMPOSITION FOR STEREOLITHOGRAPHY

(71) Applicant: KURARAY NORITAKE DENTAL INC., Kurashiki (JP)

(72) Inventor: Kenji Suzuki, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 137 days.

(21) Appl. No.: 16/754,440

(22) PCT Filed: Oct. 10, 2018

(86) PCT No.: PCT/JP2018/037792
§ 371 (c)(1),
(2) Date: Apr. 8, 2020

(87) PCT Pub. No.: WO2019/074015
PCT Pub. Date: Apr. 18, 2019

(65) Prior Publication Data
US 2020/0392272 A1 Dec. 17, 2020

(30) Foreign Application Priority Data
Oct. 10, 2017 (JP) .............................. JP2017-197259

(51) Int. Cl.
| C08F 220/68 | (2006.01) |
| B33Y 70/10 | (2020.01) |
| C08K 3/22 | (2006.01) |
| C08K 3/36 | (2006.01) |
| C08K 5/3475 | (2006.01) |
| B33Y 70/00 | (2020.01) |
| A61K 6/887 | (2020.01) |
| C08K 9/04 | (2006.01) |
| C08F 2/44 | (2006.01) |
| C08F 2/48 | (2006.01) |
| A61C 13/00 | (2006.01) |
| B33Y 10/00 | (2015.01) |
| B29C 64/124 | (2017.01) |
| B29K 509/02 | (2006.01) |

(52) U.S. Cl.
CPC ........ *C08F 220/68* (2013.01); *A61C 13/0013* (2013.01); *A61K 6/887* (2020.01); *B33Y 70/00* (2014.12); *B33Y 70/10* (2020.01); *C08F 2/44* (2013.01); *C08F 2/48* (2013.01); *C08K 3/22* (2013.01); *C08K 3/36* (2013.01); *C08K 5/3475* (2013.01); *C08K 9/04* (2013.01); *B29C 64/124* (2017.08); *B29K 2509/02* (2013.01); *B33Y 10/00* (2014.12); *C08K 2003/2213* (2013.01); *C08K 2003/2227* (2013.01); *C08K 2003/2237* (2013.01); *C08K 2003/2241* (2013.01); *C08K 2003/2244* (2013.01); *C08K 2003/2296* (2013.01); *C08K 2201/003* (2013.01); *C08K 2201/011* (2013.01); *C08K 2201/014* (2013.01)

(58) Field of Classification Search
CPC ..... C08F 2/46; C08F 2/48; C08F 2/50; A61K 6/887; C08L 33/10; C08L 33/08; C08K 3/22; C08K 2201/005; C08K 2201/014
See application file for complete search history.

(56) References Cited

U.S. PATENT DOCUMENTS

| 4,839,401 | A | * | 6/1989 | Waknine ................ A61K 6/887 522/75 |
| 6,426,373 | B1 | * | 7/2002 | Stange .................. A61K 6/893 523/116 |
| 9,456,963 | B2 | * | 10/2016 | Lee .................... A61C 13/0013 |
| 2013/0172441 | A1 | | 7/2013 | Takahata et al. |
| 2014/0131908 | A1 | * | 5/2014 | Sun ........................ B33Y 70/00 264/16 |
| 2014/0167300 | A1 | | 6/2014 | Lee |
| 2014/0239527 | A1 | | 8/2014 | Lee |
| 2016/0184189 | A1 | | 6/2016 | Hagiwara et al. |
| 2016/0332367 | A1 | | 11/2016 | Sun et al. |
| 2017/0056298 | A1 | * | 3/2017 | Eckert ...................... A61K 6/77 |

FOREIGN PATENT DOCUMENTS

| JP | 56-144478 A | 11/1981 |
| JP | 60-247515 A | 12/1985 |
| JP | 10-30002 A | 2/1998 |
| JP | 2000-159621 A | 6/2000 |

(Continued)

OTHER PUBLICATIONS

International Search Report dated Jan. 15, 2019 in PCT/JP2018/037792 filed on Oct. 10, 2018, 2 pages.
Extended European Search Report dated Jul. 13, 2021 in European Patent Application No. 188865886.8, 9 pages.
"Ultrafine Titanium Dioxide" Titan Kogyo limited: Retrieved from the Internet: URL:http://www.titankogyo.co.jp/english/productsinformation/ultrafinetitaniumdioxide/, [retrieved on May 26, 2021], XP002803100, Jun. 24, 2021, 2 pages.
"Carbon Black Products" Mitsubishi Chemical: Retrieved from the Internet: URL:http://www.carbonblack.jp/en/product/list2_01.html, [retrieved on May 26, 2021], XP002803101, Jan. 1, 2006, 3 pages.

*Primary Examiner* — Brieann R Johnston
(74) *Attorney, Agent, or Firm* — Oblon, McClelland, Maier & Neustadt, L.L.P.

(57) ABSTRACT

The present invention provides a resin composition for stereolithography that, with its low consistency, enables easy fabrication while ensuring good shape accuracy and desirable color masking properties in the cured product. The present invention relates to a resin composition for stereolithography comprising: an 80 to 99 mass % polymerizable monomer (a); a 0.1 to 10 mass % photopolymerization initiator (b); a 0.1 to 5.0 mass % inorganic particle (c) having an average particle diameter of 5 to 200 nm; and a 0.01 to 10 mass % metal oxide particle (d) having an average particle diameter of 0.1 to 10 μm, the inorganic particle (c) being different from the metal oxide particle (d).

16 Claims, No Drawings

(56) References Cited

FOREIGN PATENT DOCUMENTS

| | | |
|---|---|---|
| JP | 2006-348210 A | 12/2006 |
| JP | 2015-43793 A | 3/2015 |
| JP | 2016-525150 A | 8/2016 |
| JP | 2017-160355 A | 9/2017 |
| WO | WO 2012/042911 A1 | 4/2012 |

\* cited by examiner

RESIN COMPOSITION FOR STEREOLITHOGRAPHY

TECHNICAL FIELD

The present invention relates to a resin composition for stereolithography. Specifically, the present invention relates to a resin composition that, with its low consistency, enables easy stereolithographical fabrication of an object while ensuring good shape accuracy and desirable color masking properties. A resin composition of the present invention is particularly suited for dental modeling materials.

BACKGROUND ART

Patent Literature 1 discloses a photo-solidification technique, a method that produces a solid object through repeated exposure of controlled, necessary amounts of light energy to a liquid light-curable resin to cure the resin layer-by-layer as it is supplied onto the previously cured layer. Patent Literature 2 proposes a basic method for practical application of this technique, and, since its proposal, many other photo-solidification techniques have been proposed.

Vat stereolithography is a technique commonly used for optical fabrication of a solid object. In this technique, a computer-controlled ultraviolet laser is selectively applied to draw the desired pattern on the surface of a liquid light-curable resin composition placed in a vat. By being cured, the resin forms a layer of a predetermined thickness, and another cured layer is continuously formed on the cured layer by applying an ultraviolet laser to the liquid light-curable resin composition supplied onto the previously cured layer in an amount necessary to form a single layer. The layering process is repeated to produce a solid object of the desired shape. This technique has attracted great interest because it enables easy and precision production of the desired solid object in a relatively short time period, even when the product has a very complex shape. Traditionally, vat stereolithography has adopted a mode whereby an object being formed is lowered down in a vat filled with a large quantity of liquid light-curable resin composition. However, this type of vat stereolithography is being replaced by what is generally called the "lifting mode", which is becoming mainstream because it requires less liquid light-curable resin composition and is less wasteful.

Solid objects produced by stereolithography are used in an increasingly wider range of applications, from simple concept models to more complex models such as test models and prototypes. This has created a demand for higher shape accuracy in these solid objects. In addition to satisfying such properties, these products are also required to have properties that are suited for their intended use. The required levels of shape accuracy (conformity) are particularly high in the field of dental materials, which are thought to greatly benefit from stereolithography because prostheses such as crowns and bridges require shapes that vary from patient to patient, aside from being complex in shape. Use of stereolithographically created solid objects for modeling applications is expanding in fabrication of crowns and bridges. In such modeling applications, the solid object needs to have high color masking properties for easy visual recognition and observation of its surface, and inorganic particles are typically added to improve color masking properties. However, a drawback of adding inorganic particles is that it increases viscosity, and makes fabrication difficult. Another drawback is that inorganic particles block light. This leads to poor shape accuracy. The viscosity increase becomes even more problematic in lifting mode because the liquid, which is used in smaller quantities in this mode, has trouble reaching the surface of the object being created.

Against this background, for example, Patent Literature 3 proposes a technique that mixes a specific amount of inorganic fine particles to enable appropriate fluidity and curability to be imparted to a liquid composition for vat stereolithography.

CITATION LIST

Patent Literature

Patent Literature 1: JP 56(1981)-144478 A
Patent Literature 2: JP 60(1985)-247515 A
Patent Literature 3: JP 2006-348210 A

SUMMARY OF INVENTION

Technical Problem

None of the photo-solidification resin compositions described in Patent Literatures 1 to 3 is specifically stated to be applicable to materials that require strong color masking properties, such as in dental modeling materials.

It is accordingly an object of the present invention to provide a resin composition for stereolithography that, with its low consistency, enables easy fabrication while ensuring good shape accuracy and desirable color masking properties in the cured product. Another object of the present invention is to provide a resin composition for stereolithography suited for dental modeling materials.

Solution to Problem

Specifically, the present invention relates to the following:
[1] A resin composition for stereolithography comprising:
 an 80 to 99 mass % polymerizable monomer (a);
 a 0.1 to 10 mass % photopolymerization initiator (b);
 a 0.1 to 5.0 mass % inorganic particle (c) having an average particle diameter of 5 to 200 nm; and
 a 0.01 to 10 mass % metal oxide particle (d) having an average particle diameter of 0.1 to 10 µm,
 the inorganic particle (c) being different from the metal oxide particle (d);
[2] The resin composition for stereolithography of [1], wherein the inorganic particle (c) comprises silica or aluminum oxide;
[3] The resin composition for stereolithography of [1] or [2], wherein the metal oxide particle (d) comprises at least one metal oxide selected from the group consisting of titanium oxide, aluminum oxide, zirconium oxide, zinc oxide, and cerium oxide;
[4] The resin composition for stereolithography of [1] or [2], wherein the metal oxide particle (d) comprises at least one metal oxide selected from the group consisting of titanium oxide, aluminum oxide, and zirconium oxide;
[5] The resin composition for stereolithography of any one of [1] to [4], wherein the metal oxide particle (d) has an average particle diameter of 0.2 to 7.5 µm;
[6] The resin composition for stereolithography of any one of [1] to [5], wherein the inorganic particle (c) and the metal oxide particle (d) have a mass ratio of 2:1 to 30:1;
[7] The resin composition for stereolithography of any one of [1] to [6], wherein the inorganic particle (c) and the metal oxide particle (d) have an average particle diameter ratio of 1:1.5 to 1:2,000;

[8] The resin composition for stereolithography of any one of [1] to [7], wherein the resin composition further comprises an organic ultraviolet absorber (e);

[9] The resin composition for stereolithography of [8], wherein the organic ultraviolet absorber (e) is a benzotriazole compound;

[10] The resin composition for stereolithography of any one of [1] to [9], wherein the inorganic particle (c) is surface-treated with a surface treatment agent;

[11] The resin composition for stereolithography of any one of [1] to [10], wherein the polymerizable monomer (a) comprises at least one metal oxide selected from the group consisting of a (meth)acrylate polymerizable monomer and a (meth)acrylamide polymerizable monomer;

[12] The resin composition for stereolithography of any one of [1] to [11], wherein the polymerizable monomer (a) comprises a bifunctional(meth)acrylate polymerizable monomer;

[13] The resin composition for stereolithography of any one of [1] to [12], wherein the resin composition is for lifting-mode vats;

[14] A dental material comprising a cured product of the resin composition for stereolithography of any one of [1] to [13];

[15] A dental modeling material comprising a cured product of the resin composition for stereolithography of any one of [1] to [13]; and

[16] A method for stereolithographically producing a solid object with the resin composition for stereolithography of any one of [1] to [13].

Advantageous Effects of Invention

A resin composition for stereolithography of the present invention, with its low consistency, enables easy fabrication while ensuring good shape accuracy desirable color masking properties in the cured product. A resin composition for stereolithography of the present invention is suited for various types of dental materials, particularly dental modeling materials.

DESCRIPTION OF EMBODIMENTS

A resin composition for stereolithography of the present invention comprises: a polymerizable monomer (a); a photopolymerization initiator (b); an inorganic particle (c) having an average particle diameter of 5 to 200 nm; and a metal oxide particle (d) having an average particle diameter of 0.1 to 10 μm, the inorganic particle (c) being different from the metal oxide particle (d). In the present specification, the upper limits and lower limits of numeric ranges (ranges of, for example, contents of components, values calculated from components, and values of physical properties) can be combined appropriately.

Polymerizable Monomer (a)

Preferred for use as the polymerizable monomer (a) used in a resin composition for stereolithography of the present invention is a radical polymerizable monomer. Specific examples of the radical polymerizable monomer as polymerizable monomer (a) include (meth)acrylate polymerizable monomers; (meth)acrylamide polymerizable monomers; esters of acids such as α-cyanoacrylic acid, (meth)acrylic acid, α-halogenated acrylic acid, crotonic acid, cinnamic acid, sorbic acid, maleic acid, and itaconic acid; vinyl esters; vinyl ethers; mono-N-vinyl derivatives; and styrene derivatives. In view of curability, (meth)acrylate polymerizable monomers and (meth)acrylamide polymerizable monomers are preferred. These may be used alone, or two or more thereof may be used in combination. For advantages such as low consistency for easy fabrication, good shape accuracy, and desirable color masking properties, preferred as polymerizable monomer (a) are polymerizable monomers having no acidic group, more preferably (meth)acrylate polymerizable monomers having no acidic group, and (meth)acrylamide polymerizable monomers having no acidic group.

Examples of the polymerizable monomer (a) in the present invention include monofunctional monomers having a single polymerizable group, and polyfunctional monomers having a plurality of polymerizable groups.

Examples of monofunctional (meth)acrylate polymerizable monomers include 2-hydroxyethyl(meth)acrylate, 2-hydroxypropyl(meth)acrylate, 3-hydroxypropyl(meth)acrylate, 4-hydroxybutyl(meth)acrylate, 6-hydroxyhexyl(meth)acrylate, 10-hydroxydecyl(meth)acrylate, propylene glycol mono(meth)acrylate, glycerol mono(meth)acrylate, erythritol mono(meth)acrylate, methyl(meth)acrylate, ethyl(meth)acrylate, propyl(meth)acrylate, isopropyl(meth)acrylate, n-butyl(meth)acrylate, sec-butyl(meth)acrylate, t-butyl(meth)acrylate, isobutyl(meth)acrylate, n-hexyl(meth)acrylate, cyclohexyl(meth)acrylate, lauryl(meth)acrylate, cetyl(meth)acrylate, stearyl(meth)acrylate, isobornyl(meth)acrylate, benzyl(meth)acrylate, phenyl(meth)acrylate, 2,3-dibromopropyl(meth)acrylate, 3-(meth)acryloyloxypropyltrimethoxysilane, 11-(meth)acryloyloxyundecyltrimethoxysilane, and (meth)acrylamide. Examples of monofunctional (meth)acrylamide polymerizable monomers include N-(meth)acryloylmorpholine, N,N-dimethyl(meth)acrylamide, N,N-diethyl(meth)acrylamide, N,N-di-n-propyl(meth)acrylamide, N,N-di-n-butyl(meth)acrylamide, N,N-di-n-hexyl(meth)acrylamide, N,N-di-n-octyl(meth)acrylamide, N,N-di-2-ethylhexyl(meth)acrylamide, N-hydroxyethyl(meth)acrylamide, and N,N-(dihydroxyethyl)acrylamide. These may be used alone, or two or more thereof may be used in combination. In view of desirable curability, preferred are (meth)acrylamide polymerizable monomers, more preferably N-(meth)acryloylmorpholine, N,N-dimethyl(meth)acrylamide, and N,N-diethyl(meth)acrylamide.

Examples of the polyfunctional monomers include aromatic bifunctional polymerizable monomers, aliphatic bifunctional polymerizable monomers, and tri- and higher-functional polymerizable monomers.

Examples of the aromatic bifunctional polymerizable monomers include 2,2-bis((meth)acryloyloxyphenyl)propane, 2,2-bis[4-(3-acryloyloxy)-2-hydroxypropoxyphenyl]propane, 2,2-bis[4-(3-methacryloyloxy)-2-hydroxypropoxyphenyl]propane (commonly known as "Bis-GMA"), 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromellitate. These may be used alone, or two or more thereof may be used in combination.

In view of desirable curability and the desirable strength of the cured product, preferred are 2,2-bis[4-(3-methacryloyloxy)-2-hydroxypropoxyphenyl]propane, and 2,2-bis(4-(meth)acryloyloxypolyethoxyphenyl)propane. The 2,2-bis(4-(meth)acryloyloxypolyethoxyphenyl)propane is preferably 2,2-bis(4-methacryloyloxypolyethoxyphenyl)propane (a compound in which the average number of moles of ethoxy group added is 2.6; commonly known as D-2.6E).

Examples of the aliphatic bifunctional polymerizable monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, 1,2-bis(3-methacryloyloxy-2-hydroxypropoxy)ethane, and 2,2,4-trimethylhexamethylenebis(2-carbamoyloxyethyl)dimethacrylate (commonly known as UDMA). In view of desirable curability and the desirable strength of the cured product, 2,2,4-trimethylhexamethylenebis(2-carbamoyloxyethyl)dimethacrylate is preferred. These may be used alone, or two or more thereof may be used in combination.

Examples of the tri- and higher-functional polymerizable monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N'-(2,2,4-trimethylhexamethylene)bis[2-(aminocarboxy)propane -1,3-diol]tetra(meth)acrylate, and 1,7-diacryloyloxy-2,2,6,6-tetra(meth)acryloyloxymethyl-4-oxyheptane. In view of desirable curability and the desirable strength of the cured product, preferred are N,N'-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane.

When the polymerizable monomer (a) is containing a monofunctional (meth)acrylate polymerizable monomer, the content of the monofunctional (meth)acrylate polymerizable monomer is preferably 10 to 55 mass %, more preferably 15 to 50 mass %, even more preferably 15 to 45 mass % relative to total 100 mass % of polymerizable monomer (a). When the polymerizable monomer (a) is containing a bifunctional (meth)acrylate polymerizable monomer, the content of the bifunctional (meth)acrylate polymerizable monomer is preferably 50 mass % or more, more preferably 60 mass % or more, even more preferably 70 mass % or more relative to total 100 mass % of polymerizable monomer (a). In this specification, the content of a polymerizable monomer relative to total 100 mass % of polymerizable monomer components means the content of the polymerizable monomer (in mass %) of when the total amount of the polymerizable monomer components is converted to 100 mass %.

The content of polymerizable monomer (a) is 80 to 99 mass %, preferably 85 to 98.5 mass %, even more preferably 90 to 98 mass % of the total of the resin composition for stereolithography.

Photopolymerization Initiator (b)

The photopolymerization initiator (b) used in the present invention may be selected from common photopolymerization initiators used in industry, preferably from photopolymerization initiators used in dentistry.

Examples of the photopolymerization initiator (b) include (bis)acylphosphine oxides, thioxanthones or quaternary ammonium salts of thioxanthones, ketals, α-diketones, coumarins, anthraquinones, benzoin alkyl ether compounds, and α-aminoketone compounds. These may be used alone, or two or more thereof may be used in combination.

Preferably, the photopolymerization initiator (b) is at least one selected from the group consisting of (bis)acylphosphine oxides and salts thereof, and α-diketones. In this way, a resin composition for stereolithography can be obtained that has desirable photocurability both in the ultraviolet and visible regions, and that shows sufficient photocurability even when the light source is a laser such as an Ar laser or a He—Cd laser, or a lighting such as a halogen lamp, a xenon lamp, a metal halide lamp, a light emitting diode (LED), a mercury lamp, or a fluorescent lamp.

Examples of acylphosphine oxides in the (bis)acylphosphine oxides used as photopolymerization initiator (b) include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide. Examples of bisacylphosphine oxides include bis(2,6-dichlorobenzoyl)phenylphosphine oxide, bis(2,6-dichlorobenzoyl-2,5-dimethylphenylphosphine oxide, bis(2,6-dichlorobenzoyl)-4-propylphenylphosphine oxide, bis(2,6-dichlorobenzoyl-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Other examples include the compounds mentioned in JP 2000-159621A.

Particularly preferred as the (bis)acylphosphine oxides are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the α-diketones used as photopolymerization initiator (b) include diacetyl, benzyl, camphorquinone, 2,3-pentandione, 2,3-octadione, 9,10-phenanthrenequinone, 4,4'-oxybenzyl, and acenaphthenequinone. Camphorquinone is particularly preferred when the light source used is a visible-light source.

In view of the curability and other properties of the resin composition for stereolithography produced, the content of photopolymerization initiator (b) in a resin composition for stereolithography of the present invention is 0.1 to 10 mass %, preferably 0.5 mass % or more, even more preferably 1.0 mass % or more of the total of the resin composition for stereolithography. When the content of photopolymerization initiator (b) is more than 10 mass % relative to the resin composition for stereolithography, the photopolymerization initiator (b) may precipitate out of the resin composition for stereolithography when the solubility of the photopolymerization initiator itself is low. The content of photopolymerization initiator (b) is more preferably 7.5 mass % or less, even more preferably 5.0 mass % or less relative to the resin composition for stereolithography.

Inorganic Particle (c)

Examples of the inorganic particle (c) used in the present invention include quartz, silica, aluminum oxide (alumina), silica-titania, silica-titania-barium oxide, silica-zirconia, silica-alumina, aluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in combination. The inorganic particle (c) excludes those that classify as the metal oxide particle (d) described below. That is, in the resin composition for stereolithography, the metal oxide particle (d) and the inorganic particle (c) are different. However, the metal oxide particle (d) and the inorganic particle (c) may be of the same material when the inorganic particle (c) and the metal oxide particle (d) have different average particle diameters. In view of lowering consistency for easier fabrication, and improving shape accuracy and color masking properties, it is preferable that the inorganic particle (c) contain silica or aluminum oxide.

The shape of inorganic particle (c) is not particularly limited, as long as the present invention can exhibit its effects. However, the inorganic particle (c) is preferably spherical in shape in view of fluidity of the resin composition for stereolithography, and reduced damage to the container used for fabrication. In view of shape accuracy and color masking properties, the inorganic particle (c) needs to have an average particle diameter of 5 to 200 nm. The inorganic particle (c) has an average particle diameter of preferably 7.5 to 100 nm, more preferably 10 to 75 nm, even more preferably 12.5 to 50 nm.

In this specification, the average particle diameter of particles refers to average primary particle diameter, and the average particle diameter of inorganic particle (c) can be determined by light microscopy or electron microscopy. Specifically, it is convenient to use a light microscope for the measurement of particles having a particle diameter of 100 nm or more, and an electron microscope for the measurement of particles having a particle diameter of less than 100 nm. In light microscopy or electron microscopy, for example, particles may be photographed with a scanning electron microscope (Model S-4000, manufactured by Hitachi), and the size of particles (at least 200 particles) observed in a unit field of the micrograph may be measured using image-analyzing particle-size-distribution measurement software (Macview; Mountech Co., Ltd.). Here, the particle diameter is determined as an arithmetic mean value of the maximum and minimum lengths of particles, and the average primary particle diameter is calculated from the number of particles and the particle diameter.

In view of the consistency of the resin composition for stereolithography produced, and the shape accuracy and color masking properties of the cured product, the content of the inorganic particle (c) in a resin composition for stereolithography of the present invention needs to be 0.1 to 5.0 mass % of the total of the resin composition for stereolithography. The content of inorganic particle (c) is preferably 0.5 to 3.0 mass %, more preferably 1.0 to 2.99 mass %, even more preferably 1.0 to 2.5 mass %. The solid object produced cannot have sufficient color masking properties when the content of inorganic particle (c) is less than 0.1 mass %. When the content of inorganic particle (c) is more than 5.0 mass %, the consistency of the resin composition for stereolithography becomes too high to enable fabrication.

For the purpose of adjusting the miscibility of the inorganic particle (c) with the polymerizable monomer (a), the inorganic particle (c) may be optionally subjected to a surface treatment in advance, using known surface treatment agents such as acidic group-containing organic compounds; fatty acid amides such as saturated fatty acid amides, unsaturated fatty acid amides, saturated fatty acid bisamides, and unsaturated fatty acid bisamides; and organosilicon compounds such as silane coupling agents. For improved mechanical strength of the cured product through improved chemical bonding between the polymerizable monomer (a) and the inorganic particle (c), it is preferable to use an acidic group-containing organic compound for surface treatment. Examples of the acidic group-containing organic compounds include organic compounds having at least one acidic group such as a phosphoric acid group, a pyrophosphoric acid group, a thiophosphoric acid group, a phosphonic acid group, a sulfonic acid group, and a carboxylic acid group. The organic compounds having at least one acidic group are preferably organic compounds having at least one phosphoric acid group. When using two or more surface treatment agents, the surface treatment layer may be a mixture of two or more surface treatment agents, or may be a laminate of more than one surface treatment layer.

Examples of the acidic group-containing organic compounds having a phosphoric acid group(s) include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxy dodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts thereof.

The acidic group-containing organic compounds having an acidic group(s) such as a pyrophosphoric acid group, a thiophosphoric acid group, a phosphonic acid group, a sulfonic acid group, and a carboxylic acid group may be suitably selected from those mentioned in, for example, WO2012/042911.

Examples of the saturated fatty acid amides include palmitamide, stearamide, and behenamide. Examples of the unsaturated fatty acid amides include oleamide and erucamide. Examples of the saturated fatty acid bisamides include ethylenebispalmitamide, ethylenebisstearamide, and hexamethylenebisstearamide. Examples of the unsaturated fatty acid bisamides include ethylenebisoleamide, hexamethylenebisoleamide, and N,N'-dioleylsebacamide.

Examples of the organosilicon compounds include compounds represented by $R^1{}_n SiX_{4-n}$ (wherein $R^1$ is a substituted or unsubstituted hydrocarbon group having 1 to 12 carbon atoms, X is a C1 to C4 alkoxy group, a hydroxyl group, a halogen atom, or a hydrogen atom, and n is an integer of 0 to 3, where $R^1$ may be the same or different when a plurality of $R^1$ exists, and X may be the same or different when a plurality of X exists).

Specific examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl tris(β-methoxyethoxy)silane, 3,3,3-trifluoropropyltrimethoxysilane, methyl-3,3,3-trifluoropropyldimethoxysilane, β-(3,4-epoxycyclohexyl) ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-β(aminoethyl)-γ-aminopropylmethyldimethoxysilane, N-β(aminoethyl)-γ-aminopropyltrimethoxysilane, N-β(aminoethyl)-γ-aminopropyltriethoxysilane, γ-aminopropyltrimethoxysilane, γ-aminopropyltriethoxysilane, N-phenyl-γ-aminopropyltrimethoxysilane,
γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane [having 3 to 12 carbon atoms between the (meth)acryloyloxy group and the silicon atom; e.g., γ-methacryloyloxypropyltrimethoxysilane], and ω-(meth) acryloyloxyalkyltriethoxysilane [having 3 to 12 carbon atoms between the (meth)acryloyloxy group and the silicon atom; e.g., γ-methacryloyloxypropyltriethoxysilane]. As used herein, "(meth)acryloyloxy" is intended to include both methacryloyloxy and acryloyloxy.

Preferred are silane coupling agents having a functional group that is copolymerizable with the polymerizable monomer (a). Examples of such silane coupling agents include ω-(meth)acryloyloxyalkyltrimethoxysilane [having 3 to 12 carbon atoms between the (meth)acryloyloxy group and the silicon atom], ω-(meth)acryloyloxyalkyltriethoxysilane [having 3 to 12 carbon atoms between the (meth)acryloyloxy group and the silicon atom], vinyltrimethoxysilane, vinyltriethoxysilane, vinyltriacetoxysilane, and γ-glycidoxypropyltrimethoxysilane.

The surface treatment may be carried out using a known method, and the method is not particularly limited. For example, the surface treatment agent may be added by spraying it to the inorganic particle (c) being vigorously stirred, or the surface treatment agent may be dispersed or dissolved in a suitable solvent with the inorganic particle (c), and the solvent may be removed.

The amount of surface treatment agent is not particularly limited. For example, the surface treatment agent is preferably 0.1 to 50 parts by mass, more preferably 0.3 to 40 parts by mass, even more preferably 0.5 to 30 parts by mass relative to 100 parts by mass of the inorganic particle (c).

Metal Oxide Particle (d)

The metal oxide particle (d) used in the present invention preferably contains at least one metal oxide selected from the group consisting of titanium oxide, aluminum oxide, zirconium oxide, zinc oxide, and cerium oxide, and more preferably contains at least one metal oxide selected from the group consisting of titanium oxide, aluminum oxide, and zirconium oxide. The content of the metal oxide in the metal oxide particle (d) is not particularly limited, as long as the metal oxide is contained as a main component. However, the metal oxide content is preferably 50 mass % or more, more preferably 70 mass % or more, even more preferably 80 mass % or more, particularly preferably 90 mass % or more. The metal oxide content in the metal oxide particle (d) may be 100 mass %. The metal oxides may be used alone, or two or more thereof may be used in combination. In view of improving shape accuracy and color masking properties, preferred are titanium oxide and aluminum oxide. Increasing the content of metal oxide particles to improve color masking properties results in decrease of shape accuracy because increased numbers of metal oxide particles lowers transmissivity for an active energy beam such as a laser, and causes the active energy rays to scatter. The inorganic particle (c) needs to be contained in large quantity if color masking properties were to be increased with the inorganic particle (c) alone. In this case, the viscosity increases. In a resin composition for stereolithography of the present invention, the inorganic particle (c) is used with the metal oxide particle (d). Presumably, this increases the surface irregularities of the composition (ink), and improves the color masking properties, probably because of the composition being perceived as cloudy despite the small contents of inorganic particle (c) and metal oxide particle (d). By using inorganic particle (c) and metal oxide particle (d) in combination, it is also possible to ensure transmissivity for an active energy beam such as a laser, allowing the metal oxide particle (d) to be used in reduced amounts. This should explain the improved shape accuracy and desirable color masking properties satisfied at the same time.

In order to ensure color masking properties, the metal oxide particle (d) needs to have an average particle diameter of 0.1 to 10 μm. The average particle diameter of metal oxide particle (d) is preferably 0.2 to 7.5 μm, more preferably 0.3 to 5.0 μm, even more preferably 0.4 to 3.0 μm, particularly preferably 0.5 to 1.0 μm. A laser diffraction scattering method can be conveniently used for the average particle diameter measurement of metal oxide particle (d). For the measurement using a laser diffraction scattering method, for example, a laser diffraction particle size distribution analyzer (SALD-2100, manufactured by Shimadzu Corporation) may be used with a 0.2% sodium hexametaphosphate aqueous solution used as dispersion medium.

In view of shape accuracy and color masking properties, the content of metal oxide particle (d) in a resin composition for stereolithography of the present invention needs to be 0.01 to 10 mass % of the total of the resin composition for stereolithography. The content of metal oxide particle (d) is preferably 0.05 to 5 mass %, more preferably 0.1 to 1.0 mass %. The solid object produced cannot have sufficient color masking properties when the content of metal oxide particle (d) is less than 0.01 mass %. When the content of metal oxide particle (d) is more than 10 mass %, the color masking properties of the resin composition for stereolithography become too high to enable fabrication. In view of shape accuracy and color masking properties, the content of metal oxide particle (d) in a resin composition for stereolithography of the present invention is preferably 0.01 to 5 parts by mass, more preferably 0.05 to 3 parts by mass relative to 100 parts by mass of the polymerizable monomer (a).

For the purpose of adjusting the miscibility of the metal oxide particle (d) with the polymerizable monomer (a), the metal oxide particle (d) may be used after a surface treatment. In this case, preferred embodiments, including the surface treatment agent and the surface treatment method, are the same as those described above in conjunction with the inorganic particle (c).

In view of lowering consistency for easy fabrication, and providing good shape accuracy and improving the color masking properties of the cured product, the mass ratio of inorganic particle (c) to metal oxide particle (d) is preferably 2:1 to 30:1, more preferably 3:1 to 20:1, even more preferably 5:1 to 15:1.

Preferably, the inorganic particle (c) has an average particle diameter larger than the average particle diameter of the metal oxide particle (d). In view of lowering consistency for easy fabrication, and providing good shape accuracy and improving the color masking properties of the cured product, the average particle diameter ratio of inorganic particle (c) to metal oxide particle (d) is preferably 1:1.5 to 1:2,000, more preferably 1:3 to 1:500, even more preferably 1:5 to 1:100.

Organic Ultraviolet Absorber (e)

For improved shape accuracy, a resin composition for stereolithography of the present invention preferably comprises an organic ultraviolet absorber (e).

Examples of the organic ultraviolet absorber (e) include benzotriazole compounds, benzophenone compounds, and thiophene compounds. Preferred as the benzotriazole compounds are compounds containing a hydroxyl group attached at position 2 of an aromatic ring bound to a nitrogen atom of the triazole structure. More preferred for improved shape accuracy are compounds containing a hydroxyl group attached at position 2 of an aromatic ring bound to a nitrogen atom of the triazole structure, and having a C1 to C10 alkyl group at position 3 and/or 5 of the aromatic ring. Examples of the benzotriazole compounds include 2-(2-hydroxy-5-methylphenyl)benzotriazole (TINUVIN P), 2-(2-hydroxy-5-tert-octylphenyl)benzotriazole (TINUVIN 329), 2-(2'-hydroxy-3',5'-di-tert-butylphenyl)benzotriazole, 2-(2'-hydroxy-5'-tert-butylphenyl)benzotriazole, 2-(2'-hydroxy-3'-tert-butyl-5'-methylphenyl)benzotriazole, 2-(2'-hydroxy-3',5'-di-tert-amylphenyl)benzotriazole, 2-(2'-hydroxy-3'-tert-butyl-5'-methylphenyl)benzotriazole, 2-(2'-hydroxy-3'-tert-butyl-5'-methylphenyl)-5-chlorobenzotriazole, and 2-(2'-hydroxy-3',5'-di-tert-butylphenyl)-5-chlorobenzotriazole. Examples of the benzophenone compounds include 2,4-dihydroxybenzophenone, 2-hydroxy-4-methoxybenzophenone, 2-hydroxy-4-n-octoxybenzophenone, 2-hydroxy-4-(dodecyloxy)benzophenone, 2-hydroxy-4-(octadecyloxy)benzophenone, 2,2'-dihydroxy-4-methoxybenzophenone, and 2,2'-dihydroxy-4,4'-dimethoxybenzophenone. Examples of the thiophene compounds include thiophene compounds such as 2,5-bis(5-t-butyl-2-benzooxazolyl)thiophene. In view of more desirable shape accuracy, preferred are benzotriazole compounds.

The organic ultraviolet absorber (e) may be used alone, or two or more thereof may be used in combination. The content of the organic ultraviolet absorber (e) is preferably 0.001 to 10 mass %, more preferably 0.01 to 5 mass %, even more preferably 0.02 to 2 mass % of the total of the resin composition for stereolithography.

A resin composition for stereolithography of the present invention is not particularly limited, as long as it contains the polymerizable monomer (a), the photopolymerization initiator (b), the inorganic particle (c), and the metal oxide particle (d). A resin composition for stereolithography of the present invention may optionally contain the organic ultraviolet absorber (e), and, for example, may additionally contain other components. The content of such other components in the resin composition for stereolithography (specifically, components other than the polymerizable monomer (a), the photopolymerization initiator (b), the inorganic particle (c), the metal oxide particle (d), and the optionally contained organic ultraviolet absorber (e)) may be less than 3 mass %, less than 2 mass %, or less than 1 mass %. A resin composition for stereolithography of the present invention may be produced using a known method.

A resin composition for stereolithography of the present invention may contain a polymerization accelerator to improve photocurability, provided that addition of a polymerization accelerator is not detrimental to the gist of the present invention. Examples of the polymerization accelerator include ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-N,N-dimethylaminobenzoate, 4-(N,N-dimethylamino)benzophenone, and butyl 4-(N,N-dimethylamino)benzoate. In view of imparting desirable curability to the resin composition for stereolithography, preferred is at least one selected from the group consisting of ethyl 4-(N,N-dimethylamino)benzoate, n-butoxyethyl 4-(N,N-dimethylamino)benzoate, and 4-(N,N-dimethylamino)benzophenone.

A resin composition for stereolithography of the present invention may contain a known stabilizer, in order to inhibit deterioration, or to adjust photocurability. Examples of such stabilizers include polymerization inhibitors, and antioxidants.

Examples of the polymerization inhibitors include hydroquinone, hydroquinone monomethyl ether, dibutylhydroquinone, dibutylhydroquinone monomethyl ether, t-butyl catechol, 2-t-butyl-4,6-dimethylphenol, 2,6-di-t-butylphenol, and 3,5-di-t-butyl-4-hydroxytoluene. The polymerization inhibitor content is preferably 0.001 to 1.0 parts by mass relative to total 100 parts by mass of the polymerizable monomer (a).

A resin composition for stereolithography of the present invention may contain a known additive, in order to adjust color or paste characteristics. Examples of such additives include pigments, dyes, organic solvents, and thickeners.

A resin composition for stereolithography of the present invention can be suitably used as a resin composition for vat stereolithography employing lifting mode. When used for vat stereolithography employing lifting mode, a resin composition for stereolithography of the present invention, with its low consistency, enables easy fabrication while ensuring good shape accuracy and desirable color masking properties in the cured product. This makes the resin composition for stereolithography of the present invention suitable for various dental materials, particularly dental modeling materials.

A resin composition for stereolithography of the present invention, with its low consistency, enables easy fabrication while ensuring good shape accuracy and desirable color masking properties in the cured product. Accordingly, a resin composition for stereolithography of the present invention can be used in applications where such advantages can be exploited. As an example, a resin composition for stereolithography of the present invention can be used to produce a variety of solid objects by photo-solidification, and is particularly suited for fabrication of dental materials, most suitably dental modeling materials.

Another embodiment of the present invention is a method for producing a solid object by stereolithography (hereinafter, also referred to as "photo-solidification") using any of the resin compositions for stereolithography described above. The photo-solidification is preferably vat photo-solidification employing lifting mode.

In photo-solidification using a resin composition for stereolithography of the present invention, any known photo-solidification method and device may be used. In the present invention, the light energy used to cure the resin is preferably an active energy beam. As used herein, "active energy beam" means an energy ray capable of curing a light-curable resin composition, and includes, for example, ultraviolet light, an electron beam, X-rays, radiant rays, and high-frequency waves. For example, the active energy beam may be ultraviolet light of 300 to 400 nm wavelengths. The light source of active energy beam may be, for example, a laser such as an Ar laser and a He—Cd laser; or a lighting such as a halogen lamp, a xenon lamp, a metal halide lamp, an LED, a mercury lamp, and a fluorescent lamp. Lasers are particularly preferred. When the light source is a laser, the fabrication time can be reduced by increasing the energy level, and a solid object of high shape accuracy can be obtained by taking advantage of the desirable convergence of a laser beam.

Photo-solidification using a resin composition for stereolithography of the present invention may use any known method and any known stereolithography system, and the method and device are not particularly limited, as mentioned above. However, a typical example of the lifting-mode vat photo-solidification preferred for use in the present invention is a method that produces a solid object of the desired shape through a repeated procedure that includes a step of forming a cured layer by selectively applying an active energy beam to the photo-solidification resin composition to obtain a cured layer having a desired pattern, and a step of lifting the cured layer and continuously forming another cured layer by similarly applying an active energy beam to the uncured, liquid photo-solidification resin composition supplied. The resulting solid object may be used as it is, or may be used after improving the mechanical characteristics, shape stability, or other properties by post-curing the product under applied light or heat.

The present invention encompasses combinations of the foregoing features, provided that such combinations made in various forms within the technical idea of the present invention can produce the effects of the present invention.

EXAMPLES

The following describes the present invention in greater detail by way of Examples. It should be noted that the present invention is in no way limited by the following Examples, and various changes may be made by a person with ordinary skill in the art within the technical idea of the present invention. The components used for the resin compositions for stereolithography of Examples and Comparative Example are listed and described below with the abbreviations used.

Polymerizable Monomer (a)

(a)-1: UDMA (2,2,4-trimethylhexamethylenebis(2-carbamoyloxyethyl)dimethacrylate (manufactured by Kyoeisha Chemical Co., Ltd.))

(a)-2: Bis-GMA (2,2-bis[4-(3-methacryloyloxy)-2-hydroxypropoxyphenyl]propane (manufactured by Shin-Nakamura Chemical Co., Ltd.))

(a)-3: TEGDMA (triethylene glycol dimethacrylate (manufactured by Shin-Nakamura Chemical Co., Ltd.))

Photopolymerization Initiator (b)

(b)-1: TPO (2,4,6-trimethylbenzoyldiphenylphosphine oxide)

Inorganic Particle (c)

Inorganic particle (c)-1: Colloidal silica powder surface-treated with dimethyldichlorosilane (AEROSIL® R972, manufactured by Nippon Aerosil Co., Ltd.; average particle diameter 16 nm (spherical))

Inorganic Particles (c)-2 and (c)-3: Inorganic particles produced by the methods described below Inorganic Particle (c)-2: Silica powder treated with 3-methacryloyloxypropyltrimethoxysilane A 500-mL one-neck eggplant flask was charged with 100 g of a colloidal silica powder (AEROSIL® OX50, manufactured by Nippon Aerosil Co., Ltd.), 0.5 g of 3-methacryloyloxypropyltrimethoxysilane (Shin-Etsu Silicone® Silane Coupling Agent KBM-503, manufactured by Shin-Etsu Chemical Co., Ltd.) (0.5 parts by mass relative to 100 parts by mass of the core filler), and 200 mL of toluene, and the mixture was stirred at room temperature for 2 hours. After removing tolune by distillation under reduced pressure, the mixture was vacuum dried at 40° C. for 16 hours, and at 90° C. for 3 hours to obtain a silica powder treated with 3-methacryloyloxypropyltrimethoxysilane [inorganic particle (c)-2]. The inorganic particle (c)-2 was photographed with a scanning electron microscope (Model S-4000, manufactured by Hitachi), and the size of particles (at least 200 particles) observed in a unit field of the micrograph was measured using image-analyzing particle-size-distribution measurement software (Macview; Mountech Co., Ltd.). The particles had an average primary particle diameter of 40 nm (spherical).

Inorganic Particle (c)-3: Alumina powder treated with 10-methacryloyloxydecyl dihydrogen phosphate A 500-mL one-neck eggplant flask was charged with 100 g of an alumina powder (AEROXIDE® Alu C, manufactured by Nippon Aerosil Co., Ltd.), 0.5 g of 10-methacryloyloxydecyl dihydrogen phosphate (manufactured by Toho Chemical Industry Co., Ltd.), and 200 mL of toluene, and the mixture was stirred at room temperature for 2 hours. After removing tolune by distillation under reduced pressure, the mixture was vacuum dried at 40° C. for 16 hours, and at 90° C. for 3 hours to obtain an alumina powder surface-treated with 10-methacryloyloxydecyl dihydrogen phosphate [inorganic particle (c)-3]. The inorganic particle (c)-3 was photographed with a scanning electron microscope (Model S-4000, manufactured by Hitachi), and the size of particles (at least 200 particles) observed in a unit field of the micrograph was measured using image-analyzing particle-size-distribution measurement software (Macview; Mountech Co., Ltd.). The particles had an average primary particle diameter of 25 nm (spherical).

Metal Oxide Particle (d)

Metal oxide particle (d)-1: Titanium oxide powder (Japanese Pharmacopoeia titanium oxide, manufactured by Wako Pure Chemical Industries, Ltd.; average particle diameter 0.5 µm)

Metal oxide particle (d)-2: Aluminum oxide powder (manufactured by Admatechs under the product name "Alumina"; average particle diameter 0.7 µm)

Metal oxide particle (d)-3: Zirconium oxide powder (manufactured by Soegawa Rikagaku under the product name "Zirconium Oxide"; average particle diameter 1.0 µm)

Organic Ultraviolet Absorber (e)

(e)-1: HOB (2-(2-hydroxy-5-tert-octylphenyl)benzotriazole)

Polymerization Inhibitor

BHT: 3,5-Di-t-butyl-4-hydroxytoluene

Examples 1 to 7 and Comparative Examples 1 to 5

The components were mixed under ordinary temperature (20° C.±15° C., JIS (Japanese Industrial Standards) Z 8703: 1983) in the amounts shown in Tables 1 and 2 to prepare inks as resin compositions for stereolithography of Examples 1 to 7 and Comparative Examples 1 to 5.

Ease of Fabrication

1. Fabricability

The inks of Examples and Comparative Examples were each used to produce a cube-shaped solid object measuring 10.000 mm each side, using a stereolithography device (DigitalWax® 020D, manufactured by DWS). The solid objects were visually inspected for fabricability by checking for defects such as break-offs, gaps, and damage to container.

2. Consistency

A PET film measuring 50 mm each side and 0.05 mm in thickness was placed on a flat surface, and 0.5 ml of each ink from Examples and Comparative Examples was dropped at the center of the film. The ink was allowed to stand for 10 minutes in a room held at a constant temperature of 25° C. The ink diameter was then calculated by taking an average of the maximum diameter (major axis) and the minimum diameter (minor axis) of the circularly spread ink. For calculations of ink diameter, this procedure was carried out for three ink samples from each Example and Comparative Example. The mean value of the three measurements was used as a measure of consistency. Larger consistency values mean that the ink is more flowable, and is easier to fabricate. In the test, inks with a consistency value of 30 mm or more, preferably 40 mm or more, were regarded as having high fluidity, and being easily fabricable.

Shape Accuracy

The inks of Examples and Comparative Examples were used to prepare cube-shaped solid objects measuring 10.000 mm each side, using a stereolithography device (DigitalWax® 020D, manufactured by DWS). The solid object was washed with ethanol, and was measured for dimensions (unit: mm) using a micrometer after removing unpolymerized monomers. Shape accuracy was calculated using the following formula. As a rule, a modeling material created from an ink with a shape accuracy (dimensional error) of 1.0% or less shows good shape accuracy, and can produce crowns and bridges having good conformity when fabricated into such appliances. Preferably, the shape accuracy is 0.80% or less.

$$\text{Shape precision (\%)} = \frac{|(\text{measured dimensions}) - 10.0|}{10.0} \times 100 \quad \text{[Math. 1]}$$

Color Masking Properties

The inks of Examples and Comparative Examples were used to produce disc-shaped solid objects measuring 15.0 mm in diameter and 1.0 mm in thickness, using a stereolithography device (DigitalWax® 020D, manufactured by DWS). The solid object was washed with ethanol, and, after removing unpolymerized monomers, further polymerized for 90 seconds to obtain a cured product, using a dental LED polymerizer α-Light V (manufactured by Morita Tokyo MFG. Corp.). The cured product was polished first with a silicon carbide paper #1000, and then with a dental lapping film (manufactured by 3M Japan). The product was then measured for transparency ΔL using a spectrophotometer (Spectrophotometer CM-3610d, manufactured by Konica Minolta; measurements were conducted in compliance with JIS Z 8722: 2009, Condition c; D65 illuminant). Here, transparency ΔL was measured as an index of evaluation of color masking properties. Transparency ΔL is defined by the following formula. A transparency ΔL of 15 or less is needed to ensure high color masking properties. The results are presented in Tables 1 and 2.

$$\Delta L = L^*W - L^*B$$

In the formula, L*W represents the lightness L* in the L*a*b* color system measured against a white background according to JIS Z 8781-4: 2013, and L*B represents the lightness L* in the L*a*b* color system measured against a black background.

TABLE 1

| | | | Example | | | | | | |
|---|---|---|---|---|---|---|---|---|---|
| | | | 1 | 2 | 3 | 4 | 5 | 6 | 7 |
| Raw materials (mass %) | UDMA | (a)-1 | 45.25 | 45.8 | 44.45 | 45.25 | 45.25 | 45.25 | 45.25 |
| | Bis-GMA | (a)-2 | 25 | 25 | 25 | 25 | 25 | 25 | 25 |
| | TEGDMA | (a)-3 | 25 | 25 | 25 | 25 | 25 | 25 | 25 |
| | TPO | (b)-1 | 2.0 | 2.0 | 2.0 | 2.0 | 2.0 | 2.0 | 2.0 |
| | Inorganic particle | (c)-1 | 2.0 | 1.5 | 2.5 | | | 2.0 | 2.0 |
| | Inorganic particle | (c)-2 | | | | 2.0 | | | |
| | Inorganic particle | (c)-3 | | | | | 2.0 | | |
| | Metal oxide particle | (d)-1 | 0.20 | 0.15 | 0.50 | 0.20 | 0.20 | | |
| | Metal oxide particle | (d)-2 | | | | | | 0.20 | |
| | Metal oxide particle | (d)-3 | | | | | | | 0.20 |
| | HOB | (e)-1 | 0.5 | 0.5 | 0.5 | 0.5 | 0.5 | 0.5 | 0.5 |
| | BHT | | 0.05 | 0.05 | 0.05 | 0.05 | 0.05 | 0.05 | 0.05 |
| Properties | Fabricability | | Fabricable | Fabricable | Fabricable | Fabricable | Fabricable | Fabricable | Fabricable |
| | Consistency (mm) | | 45 | 48 | 42 | 43 | 43 | 44 | 43 |
| | Shape accuracy (%) | | 0.45 | 0.42 | 0.62 | 0.54 | 0.58 | 0.63 | 0.74 |
| | Transparency ΔL | | 9.5 | 13 | 7.4 | 12 | 12 | 12 | 8.5 |

TABLE 2

| | | | Comparative Example | | | | |
|---|---|---|---|---|---|---|---|
| | | | 1 | 2 | 3 | 4 | 5 |
| Raw materials (mass %) | UDMA | (a)-1 | 47.25 | 45.45 | 45.25 | 42.25 | 45.25 |
| | Bis-GMA | (a)-2 | 25 | 25 | 25 | 25 | 25 |
| | TEGDMA | (a)-3 | 25 | 25 | 25 | 25 | 25 |
| | TPO | (b)-1 | 2.0 | 2.0 | 2.0 | 2.0 | 2.0 |
| | Inorganic particle | (c)-1 | | 2.0 | 2.0 | 7.5 | |
| | Inorganic particle | 1 *1 | | | | | 2.0 |
| | Metal oxide particle | (d)-1 | 0.20 | | | 0.20 | 0.20 |
| | Metal oxide particle | 1 *2 | | | 0.20 | | |

TABLE 2-continued

|  |  |  | Comparative Example | | | | |
|---|---|---|---|---|---|---|---|
|  |  |  | 1 | 2 | 3 | 4 | 5 |
|  | HOB | (e)-1 | 0.5 | 0.5 | 0.5 | 0.5 | 0.5 |
|  | BHT |  | 0.05 | 0.05 | 0.05 | 0.05 | 0.05 |
| Properties | Fabricability |  | Fabricable | Fabricable | Fabricable | Gaps | Damage to container |
|  | Consistency (mm) |  | 48 | 46 | 45 | 24 | 26 |
|  | Shape accuracy (%) |  | 1.8 | 2.4 | 0.89 | Unmeasurable | Unmeasurable |
|  | Transparency ΔL |  | 16 | 48 | 35 | Unmeasurable | Unmeasurable |

*[1] Inorganic particle 1: Silica powder (High-Silica, manufactured by High-Silica Kogyo; average particle diameter 2.5 μm)
*[2] Metal oxide particle 1: Titanium oxide powder (TTO-51(c), manufactured by Ishihara Sangyo Kaisha, Ltd.; average particle diameter 20 nm)

As shown in Tables 1 and 2, the resin compositions for stereolithography of Examples 1 to 7 had fabricable viscosities, and showed good shape accuracy with desirable color masking properties in the cured products. Shape accuracy and color masking properties were poor in the compositions of Comparative Examples 1 to 3 that did not contain inorganic particle (c) or metal oxide particle (d). The composition of Comparative Example 4 containing an excessive amount of inorganic particle (c) had high consistency, and was not fabricable. The composition of Comparative Example 5 containing inorganic particles of large particle diameters caused damage to the container, and was not fabricable.

INDUSTRIAL APPLICABILITY

A resin composition for stereolithography of the present invention, with its low consistency, enables easy fabrication while ensuring good shape accuracy and desirable color masking properties in the cured product. A resin composition for stereolithography of the present invention is therefore suited for dental materials, particularly dental modeling materials.

The invention claimed is:

1. A resin composition, comprising:
80 to 99 mass % of a polymerizable monomer (a);
0.1 to 10 mass % of a photopolymerization initiator (b);
0.1 to 3.0 mass % of an inorganic particle (c) having an average particle diameter of from 7.5 to 100 nm; and
0.01 to 10 mass % of a metal oxide particle (d) having an average particle diameter of from 0.1 to 5.0 μm,
relative to a total amount of the resin composition,
wherein the inorganic particle (c) is different from the metal oxide particle (d),
wherein the inorganic particle (c) is surface-treated with a surface treatment agent,
wherein the inorganic particle (c) and the metal oxide particle (d) have an average particle diameter ratio of from 1:5 to 1:2,000,
wherein the inorganic particle (c) comprises at least one material selected from the group consisting of quartz, silica, aluminum oxide, silica-titania, silica-titania-barium oxide, silica-zirconia, silica-alumina, aluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass, and
wherein the metal oxide particle (d) comprises at least one metal oxide selected from the group consisting of titanium oxide, aluminum oxide, zirconium oxide, zinc oxide, and cerium oxide.

2. The resin composition according to claim 1, wherein the inorganic particle (c) comprises silica or aluminum oxide.

3. The resin composition according to claim 1, wherein the metal oxide particle (d) comprises at least one metal oxide selected from the group consisting of titanium oxide, aluminum oxide, and zirconium oxide.

4. The resin composition according to claim 1, wherein the metal oxide particle (d) has an average particle diameter of from 0.3 to 5.0 μm.

5. The resin composition according to claim 1, wherein the inorganic particle (c) and the metal oxide particle (d) have a mass ratio of from 2:1 to 30:1.

6. The resin composition according to claim 1, wherein the inorganic particle (c) and the metal oxide particle (d) have an average particle diameter ratio of from 1:5 to 1:500.

7. The resin composition according to claim 1, wherein the resin composition further comprises an organic ultraviolet absorber (e).

8. The resin composition according to claim 7, wherein the organic ultraviolet absorber (e) is a benzotriazole compound.

9. The resin composition according to claim 1, wherein the polymerizable monomer (a) comprises at least one polymerizable monomer selected from the group consisting of a (meth)acrylate polymerizable monomer and a (meth)acrylamide polymerizable monomer.

10. The resin composition according to claim 1, wherein the polymerizable monomer (a) comprises a bifunctional (meth)acrylate polymerizable monomer.

11. The resin composition according to claim 1, wherein the resin composition is suitable for stereolithography with lifting-mode vats.

12. A dental material comprising a cured product of the resin composition of claim 1.

13. A dental modeling material comprising a cured product of the resin composition of claim 1.

14. A method, comprising:
stereolithographically producing a solid object with the resin composition of claim 1.

15. The resin composition according to claim 1, wherein the content of the metal oxide particle (d) is from 0.01 mass % to 1.0 mass %.

16. The resin composition according to claim 1, wherein the average particle diameter of the inorganic particle (c) is from 7.5 to 75 nm.

* * * * *